US010426486B2

(12) United States Patent
Guo et al.

(10) Patent No.: US 10,426,486 B2
(45) Date of Patent: *Oct. 1, 2019

(54) VASO-OCCLUSIVE DEVICE DELIVERY SYSTEM

(71) Applicants: STRYKER CORPORATION, Kalamazoo, MI (US); STRYKER EUROPEAN HOLDINGS I, LLC, Kalamazoo, MI (US)

(72) Inventors: Lantao Guo, San Ramon, CA (US); Hancun Chen, San Ramon, CA (US); Richard Murphy, Sunnyvale, CA (US)

(73) Assignees: STRYKER CORPORATION, Kalamazoo, MI (US); STRYKER EUROPEAN HOLDINGS I, LLC, Kalamazoo, MI (US)

(*) Notice: Subject to any disclaimer, the term of this patent is extended or adjusted under 35 U.S.C. 154(b) by 68 days.

This patent is subject to a terminal disclaimer.

(21) Appl. No.: 15/276,174

(22) Filed: Sep. 26, 2016

(65) Prior Publication Data
US 2017/0007265 A1    Jan. 12, 2017

Related U.S. Application Data

(63) Continuation of application No. 14/206,244, filed on Mar. 12, 2014, now Pat. No. 9,451,964.
(Continued)

(51) Int. Cl.
*A61B 17/12* (2006.01)
*A61B 17/00* (2006.01)

(52) U.S. Cl.
CPC .... *A61B 17/12113* (2013.01); *A61B 17/1214* (2013.01); *A61B 17/12022* (2013.01);
(Continued)

(58) Field of Classification Search
CPC ........ A61B 17/12113; A61B 17/12022; A61B 17/1214; A61B 2017/12068
See application file for complete search history.

(56) References Cited

U.S. PATENT DOCUMENTS

| 4,994,069 A | 2/1991 | Ritchart et al. |
| 5,540,665 A * | 7/1996 | Mercado ........... A61M 5/14526 604/145 |

(Continued)

FOREIGN PATENT DOCUMENTS

| EP | 0992219 A1 | 4/2000 |
| EP | 1825823 A1 | 8/2007 |
| WO | 9209651 | 6/1992 |

OTHER PUBLICATIONS

PCT International Search Report and Written Opinion for PCT/US2014/024326, Applicant Stryker Corporation et al., filed Mar. 12, 2014, forms PCT/ISA/210 and PCT/ISA/237 (9 pages).

*Primary Examiner* — Richard G Louis
(74) *Attorney, Agent, or Firm* — Vista IP Law Group LLP

(57) ABSTRACT

A vaso-occlusive device delivery assembly includes a pusher assembly and a vaso-occlusive device detachably coupled to the pusher assembly by an attachment member is frictionally secured within a lumen of the pusher assembly. A heat generating member is disposed in the pusher assembly lumen, along with a pressure generating material, such that, when heat is generated by the heat generative device, the pressure generating material increases a pressure in the pusher assembly lumen, thereby dislodging the attachment member from the pusher assembly and detaching the vaso-occlusive device from the pusher assembly.

16 Claims, 4 Drawing Sheets

Related U.S. Application Data

(60) Provisional application No. 61/785,556, filed on Mar. 14, 2013.

(52) U.S. Cl.
CPC .... *A61B 17/12145* (2013.01); *A61B 17/1215* (2013.01); *A61B 2017/00845* (2013.01); *A61B 2017/12059* (2013.01); *A61B 2017/12068* (2013.01)

(56) References Cited

U.S. PATENT DOCUMENTS

| | | | |
|---|---|---|---|
| 2001/0027293 A1* | 10/2001 | Joshi | A61M 5/30 604/131 |
| 2004/0048940 A1* | 3/2004 | Kinoshita | C08G 18/4261 521/155 |
| 2007/0239192 A1* | 10/2007 | Litzenberg | A61B 17/12022 606/191 |
| 2010/0330027 A1* | 12/2010 | Liu | A61L 24/06 424/78.35 |
| 2014/0277094 A1 | 9/2014 | Chen et al. | |

* cited by examiner

VASO-OCCLUSIVE DEVICE DELIVERY SYSTEM

RELATED APPLICATION DATA

The present application is a continuation of pending U.S. patent application Ser. No. 14/206,244, filed Mar. 12, 2014, issued as U.S. Pat. No. 9,451,964, which claims the benefit under 35 U.S.C. § 119 to U.S. Provisional Application Ser. No. 61/785,556, filed Mar. 14, 2013. The foregoing applications are hereby incorporated by reference into the present application in its entirety.

FIELD

The field of the disclosed inventions generally relates to systems and delivery devices for implanting vaso-occlusive devices for establishing an embolus or vascular occlusion in a vessel of a human or veterinary patient. More particularly, the disclosed inventions relate to pressure actuated vaso-occlusive device delivery systems.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the pusher assembly is extended out of the distal end opening of the micro-catheter and into the aneurysm. Once in the aneurysm, segments of some vaso-occlusive devices break off to allow more efficient and complete packing. The vaso-occlusive device is then released or "detached" from the end of the pusher assembly, and the pusher assembly is withdrawn back through the catheter. Depending on the particular needs of the patient, one or more additional occlusive devices may be pushed through the catheter and released at the same site.

One well-known way to release a vaso-occlusive device from the end of the pusher assembly is through the use of an electrolytically severable junction, which is a small exposed section or detachment zone located along a distal end portion of the pusher assembly. The detachment zone is typically made of stainless steel and is located just proximal of the vaso-occlusive device. An electrolytically severable junction is susceptible to electrolysis and disintegrates when the pusher assembly is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher completes an electrolytic detachment circuit with a return electrode, and the detachment zone disintegrates due to electrolysis.

While electrolytically severable junctions have performed well, there remains a need for other systems and methods for delivery vaso-occlusive devices into vessel lumens.

SUMMARY

In one embodiment of the disclosed inventions, a vaso-occlusive device delivery assembly includes a pusher assembly and a vaso-occlusive device having an attachment member at a proximal end thereof. The pusher assembly includes an elongate body having a distal end and a pusher assembly lumen in communication with an opening in the distal end, the attachment member being frictionally secured to the pusher assembly within the pusher assembly lumen, such that the vaso-occlusive device is detachably connected to the pusher assembly. A heat generating member is disposed in the pusher assembly lumen, and a pressure generating material disposed in the pusher assembly lumen, such that, when heat is generated by the heat generative device, the pressure generating material increases a pressure in the pusher assembly lumen, thereby dislodging the attachment member from the pusher assembly and detaching the vaso-occlusive device from the pusher assembly.

In some embodiments, the heat generating member may be disposed in the distal end of the elongate body, and the pressure generating material may be adjacent to, or in contact with, the heat generating member. Alternatively or additionally, the pressure generating material may surround the heat generating member. The pressure generating material may include a solid, such as an inorganic salt hydrate, selected from the group consisting of sodium carbonate monohydrate, calcium sulfate dihydrate, calcium sulfate pentahydrate, copper sulfate pentahydrate, and sodium bicarbonate. At least a part of the pressure generating material, when heated, changes state, becoming a liquid or a gas.

In other embodiments, the pressure generating material includes a fluid. The pusher assembly and the vaso-occlusive device may be configured such that the fluid may be introduced into the pusher assembly lumen during delivery.

In some embodiments, the heat generating member is a resistive heating coil. The assembly may also include a seal disposed in the pusher assembly lumen proximal of the heat generating member such that, when the attachment member is frictionally secured to the pusher assembly within the pusher assembly lumen, the respective seal, elongate body, and attachment member define a substantially fluid tight chamber.

In some embodiments, the pusher assembly also includes a resilient retaining member frictionally secured to the attachment member within the pusher assembly lumen, where, when heat is generated by the heat generating member, the pressure generating material increases a pressure in the pusher assembly lumen, thereby deforming the resilient retaining member and detaching the vaso-occlusive device from the pusher assembly. The retaining member may be made of a deformable polymer.

In another embodiment of the disclosed inventions, a vaso-occlusive device delivery assembly includes a pusher assembly and a vaso-occlusive device defining a vaso-occlusive device lumen. The pusher assembly includes an elongate body having a distal end and a pusher assembly lumen in communication with an opening in the distal end, a tubular connecting member having an open proximal end and a closed distal end, where the open proximal end is disposed in the pusher assembly lumen at the distal end of the elongate body, a heat generating member disposed at least partially disposed in the tubular connecting member, and a pressure generating material disposed in the pusher assembly lumen. The closed distal end of the tubular connecting member is attached to the vaso-occlusive device in the vaso-occlusive device lumen such that the vaso-occlusive device is detachably connected to the pusher assembly via the tubular connecting member. The pressure generating material and the heat generating member form a substantially fluid tight seal at the open proximal end of the tubular connecting member. When heat is generated by the heat generative device, the pressure generating material increases a pressure in the tubular connecting member, thereby severing the tubular connecting member and detaching the vaso-occlusive device from the pusher assembly. In some embodiments, the pressure generating material is disposed adjacent the heat generating member.

In some embodiments, the tubular connecting member includes a detach zone, and increasing a pressure in the tubular connecting member may sever the tubular connecting member at the detach zone. The tubular connecting member may perforated at the detach zone to accelerate severance of the tubular connecting member with increased pressure in the tubular connecting member. Alternatively or additionally, the detach zone may be treated to accelerate severance of the tubular connecting member with increased pressure in the tubular connecting member. The detach zone may be thermally or mechanically weakened.

In yet another embodiment of the disclosed inventions, a vaso-occlusive device delivery assembly includes a pusher assembly and a vaso-occlusive device including an attachment member at a proximal end thereof, the attachment member being secured to the pusher assembly within the pusher assembly lumen with an interference fit, such that the vaso-occlusive device is detachably connected to the pusher assembly. The pusher assembly includes an elongate body having a distal end and a pusher assembly lumen in communication with an opening in the distal end, and a heat generating member disposed in the pusher assembly lumen. When heat is generated by the heat generative device, the a pressure in the pusher assembly lumen increases, thereby overcoming the interference fit, dislodging the attachment member from the pusher assembly, and detaching the vaso-occlusive device from the pusher assembly.

In still another embodiment of the disclosed inventions, a method of detaching a vaso-occlusive device from a pusher assembly frictionally attached thereto includes activating a heat generating member disposed in a lumen of the pusher assembly to generate heat to cause a pressure generating material to generate pressure to overcome a frictional attachment, thereby detaching the vaso-occlusive device from the pusher assembly. The generated pressure may also force the vaso-occlusive device away from the pusher assembly.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
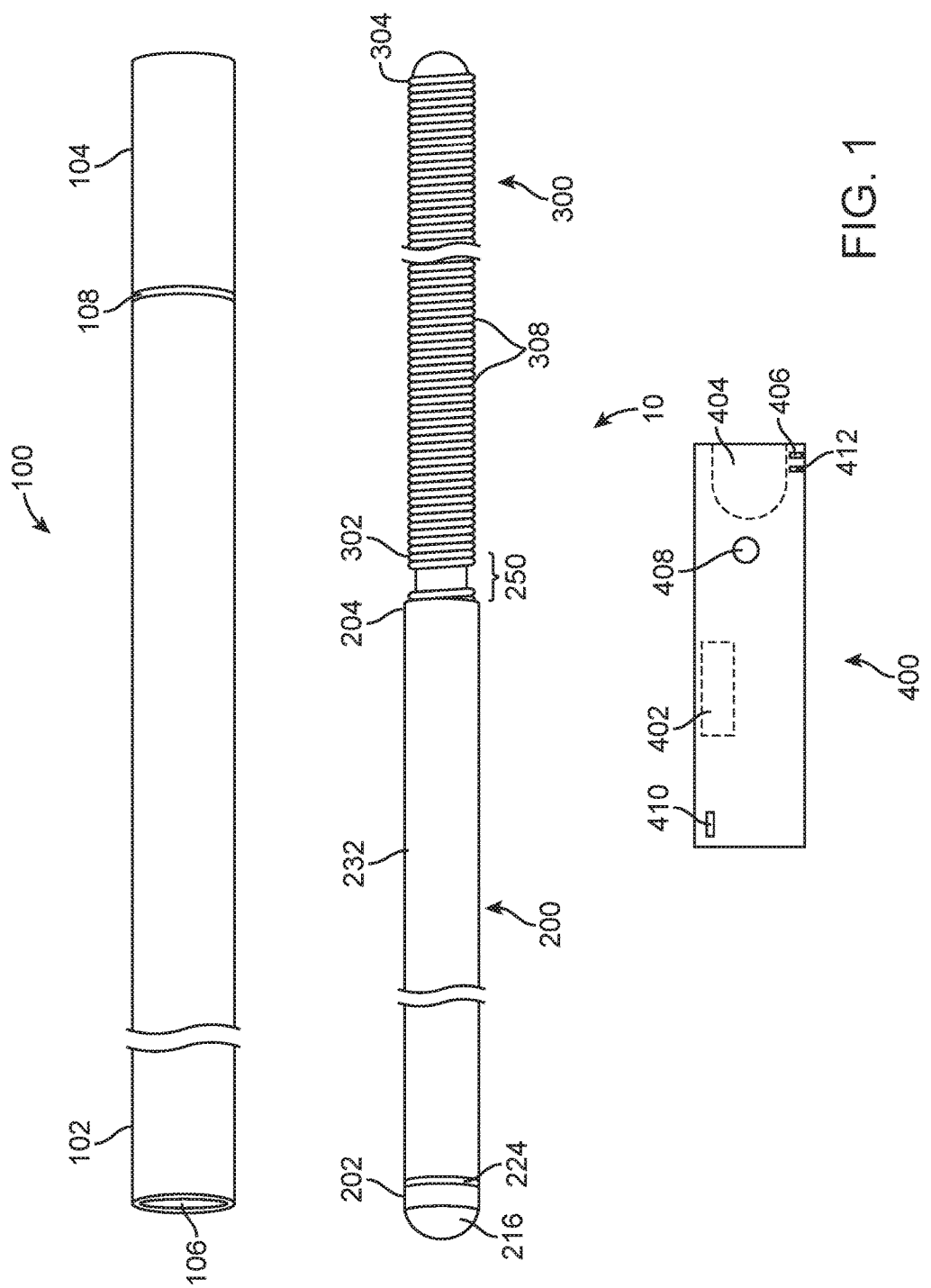
FIG. 1 is a schematic view of a vaso-occlusive device delivery system, according to one embodiment of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 illustrates a known vaso-occlusive device delivery system 10. In the system 10 illustrated in FIG. 1, the vaso-occlusive device is a vaso-occlusive coil 300. The system 10 includes a number of subcomponents or subsystems. These include a delivery catheter 100, a pusher assembly 200, a vaso-occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the pusher assembly 200 and the vaso-occlusive coil 300. Further, the lumen 106 is sized for the passage of a guidewire (not shown) which may optionally be used to properly guide the delivery catheter 100 to the appropriate delivery site.

The delivery catheter 100 may include a braided-shaft construction of stainless steel flat wire that is encapsulated or surrounded by a polymer coating. By way of non-limiting example, HYDROLENE® is a polymer coating that may be used to cover the exterior portion of the delivery catheter 100. Of course, the system 10 is not limited to a particular construction or type of delivery catheter 100 and other constructions known to those skilled in the art may be used for the delivery catheter 100. The inner lumen 106 may be advantageously coated with a lubricious coating such as PTFE to reduce frictional forces between the delivery catheter 100 and the respective pusher assembly 200 and vaso-occlusive coil 300 being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application, but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the respective pusher assembly 200 and vaso-occlusive coil 300, but generally the OD of the lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Figure 2:
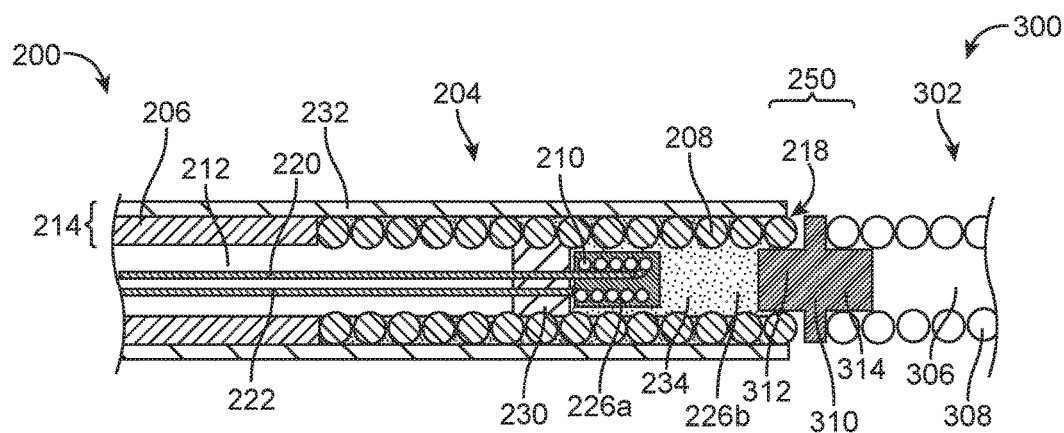
FIGS. 2-5B are detailed longitudinal cross-sectional views of vaso-occlusive device delivery systems according to various embodiments of the disclosed inventions, which depict the junction between the various pusher assemblies and vaso-occlusive devices.

As illustrated in FIGS. 1 and 2, the system 10 includes a pusher assembly 200 configured for axial movement within the lumen 106 of the delivery catheter 100. The pusher assembly 200 generally includes a proximal end 202 and a distal end 204. The pusher assembly 200 includes a pusher conduit 214, which has a proximal tubular portion 206 and a distal coil portion 208, and defines a pusher lumen 212 and a distal opening 218 in communication with the pusher lumen 212.

FIG. 2 illustrates a detailed longitudinal cross-sectional view of the junction 250 between the pusher assembly 200 and the vaso-occlusive coil 300 according to one embodiment of the disclosed inventions. Similar elements of this embodiment are identified with the same reference numbers as discussed above with respect to FIG. 1. The pusher assembly 200 includes a proximal end 202 and a distal end 204 and measures between around 184 cm to around 186 cm in length. The proximal tubular portion 206 may be formed from, for example, a flexible stainless steel hypotube. The proximal tubular portion 206 may be formed from stainless steel hypotube having an OD of 0.01325 inches and inner diameter (ID) of 0.0075 inches. The length of the hypotube section may be between around 140 cm to around 150 cm, although other lengths may also be used.

A distal coil portion 208 is joined in end-to-end fashion to the distal face of the proximal tubular portion 206. The joining may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil. One or more windings of the distal coil portion 208 may be formed from a radiopaque material, forming marker coils. For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

An outer sleeve 232 or jacket surrounds a portion of the proximal tubular portion 206 and a portion of the distal coil portion 208 of the pusher conduit 214. The outer sleeve 232 covers the interface or joint formed between the proximal tubular portion 206 and the distal coil portion 208. The outer sleeve 232 may have a length of around 50 cm to around 54 cm. The outer sleeve 232 may be formed from a polyether block amide plastic material (e.g., PEBAX 7233 lamination). The outer sleeve 232 may include a lamination of PEBAX and HYDROLENE® that may be heat laminated to the pusher assembly 200. The OD of the outer sleeve 232 may be less than 0.02 inches and advantageously less than 0.015 inches. In embodiments where the pusher conduit 214 forms the negative conductor 222, the outer sleeve 232 is removed from the very distal end of the pusher conduit 214, during manufacturing, to form an exposed negative electrical contact 224.

As shown in FIG. 2, the pusher assembly 200 further includes a heat generating member 210 disposed in its distal end 204. In the embodiment depicted in FIG. 2, the heat generating member 210 is a resistive heating coil 210. In other embodiments, the heat generating member 210 may include mechanical, inductive, magnetic, or optical mechanisms. The resistive heating coil 210 is connected to positive and negative conductors 220, 222 disposed in the pusher lumen 212. The resistive heating coil 210 can be wound from Nichrome® (nickel chromium alloy) wire, such that when a current is delivered through the resistive heating coil 210 by the positive and negative conductors 220, 222 from the power supply 400, a resistance to the current flow generates heat in the resistive heating coil 210.

The positive and negative conductors 220, 222 may be formed from an electrically conductive material such as copper wire, with an OD of around 0.00175 inches. The proximal ends of the positive and negative conductors 220, 222 are electrically connected to positive and negative electrical contacts 216, 224, respectively. As shown in FIG. 1, positive and negative electrical contacts 216, 224 are located at the proximal end of the pusher assembly 200. The positive electrical contact 216 may be formed from a metallic solder (e.g., gold) that is configured to interface with a corresponding electrical contact (not shown) in the power supply 400 (described below). The negative electrical contact 224 may be an annular ring electrode disposed on top of an electrically insulative outer sleeve 232 at the proximal end of the pusher conduit 214 (described below). The positive and negative conductors 220, 222 may be coated with an insulative coating such as polyimide except where they connect to the positive and negative electrical contacts 216, 224, respectively.

The resistive heating coil 210 is substantially surrounded by a pressure generating material 226. In some embodiments, the pressure generating material 226 is a solid 226a that becomes a liquid or a gas 226b when heated, thereby increasing the pressure in its immediate vicinity. In other embodiments, the pressure generating materials 226 may be liquids or gases. In fact, heating the air adjacent to the resistive heating coil 210 will increase its pressure.

Suitable pressure generating materials 226 include inorganic salt hydrates. The following pressure generating materials 226 release liquid water and water vapor at the indicated temperatures:

sodium carbonate monohydrate ($Na_2CO_3.H_2O$) at 100° C., calcium sulfate dihydrate ($CaSO_4.2H_2O$) at 80° C., copper sulfate pentahydrate ($CuSO_4.5H_2O$) at 100° C., and sodium bicarbonate ($NaHCO_3$) at 100° C.-200° C.

Sodium bicarbonate releases water vapor and carbon dioxide gas, according to the following reaction: $2NaHCO_3$ (s)→$CO_2$ (g)+$H_2O$ (g)+$Na_2CO_3$ (s). Other substances can also release oxygen gas. The gases produced may be minimal in quantity and readily absorbable in blood.

A proximal seal 230 is also attached to the interior surface of the pusher conduit 214 in the pusher lumen 212. The proximal seal 230 is located proximal of the resistive heating coil 210. The positive and negative conductors 220, 222 extend through the proximal seal 230 while the proximal seal 230 maintains a substantially fluid tight seal between regions proximal and distal of the proximal seal 230.

The vaso-occlusive coil 300 includes a proximal end 302, a distal end 304, and a lumen 306 extending there between. The vaso-occlusive coil 300 is made from a biocompatible metal such as platinum or a platinum alloy (e.g., platinum-tungsten alloy). The vaso-occlusive coil 300 includes a plurality of coil windings 308. The coil windings 308 are generally helical about a central axis disposed along the lumen 306 of the vaso-occlusive coil 300. The vaso-occlusive coil 300 may have a closed pitch configuration as illustrated in FIGS. 1 and 2. A tether (not shown), such as a suture, may extend from the proximal end 302 through the lumen 306 to the distal end 304 where it is connected to the distal end 304 of the vaso-occlusive coil 300.

Figure 6:
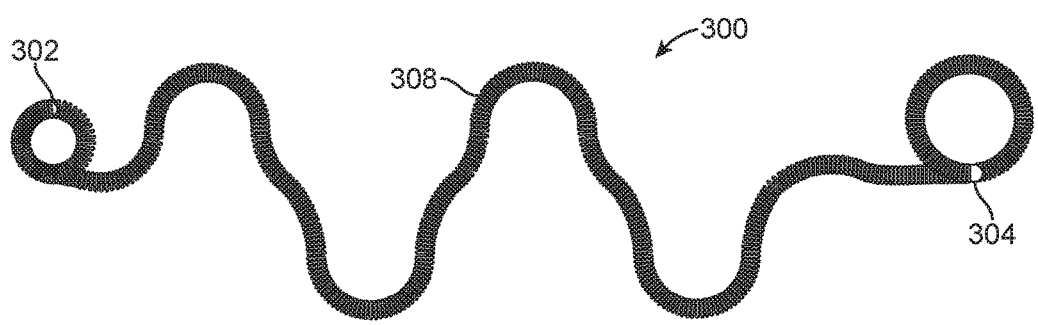
FIG. 6 is a side view of an occlusive coil in a natural state mode, illustrating one exemplary secondary configuration according to an embodiment of the disclosed inventions.

The vaso-occlusive coil 300 generally includes a straight configuration (as illustrated in FIG. 1) when the vaso-occlusive coil 300 is loaded within the delivery catheter 100. Upon release, the vaso-occlusive coil 300 generally takes a secondary shape which may include three-dimensional helical configurations. FIG. 6 illustrates one exemplary configuration of a vaso-occlusive coil 300 in a natural state. In the natural state, the vaso-occlusive coil 300 transforms from the straight configuration illustrated in, for instance, FIG. 1 into a secondary shape. The secondary shaped may include both two and three dimensional shapes of a wide variety. FIG. 6 is just one example of a secondary shape of a vaso-occlusive coil 300 and other shapes and configurations are contemplated to fall within the scope of the disclosed inventions. Also, the vaso-occlusive coil 300 may incorporate synthetic fibers (not shown) over all or a portion of the vaso-occlusive coil 300 as is known in the art. These fibers may be attached directly to coil windings 308 or the fibers may be integrated into the vaso-occlusive coil 300 using a weave or braided configuration. Of course, the system 10 described herein may be used with occlusive coils 300 or other occlusive structures having a variety of configurations, and is not limited to occlusive coils 300 having a certain size or configuration.

The vaso-occlusive coil 300 depicted in FIG. 2 includes an attachment member 310 edits proximal end 302. The attachment member 310 has proximal and distal portions 312, 314. The attachment member 310 may be molded from a deformable polymer. The distal portion 314 of the attachment member 310 is permanently attached to an interior surface of the vaso-occlusive coil 300 at the proximal end of the occlusive coil lumen 306. The distal portion 314 of the attachment member 310 may be attached to the occlusive coil with an adhesive.

The proximal portion 312 of the attachment member 310 is detachably connected (i.e., releasably attached) to an interior surface of the pusher conduit 214 with an interference fit at the distal end of the pusher lumen 212. The proximal portion 312 of the attachment member 310 has a cross-sectional area slightly larger than the cross-sectional area of the pusher lumen 212 at its distal end. The deformability of the attachment member 310 and the relative sizes of the proximal portion 312 and the pusher lumen 212 allow the proximal portion 312 to be radially and elastically compressed one inserted into the pusher lumen 212, thereby generating a radially outward force against the interior surface of the pusher conduit 214.

As shown in FIG. 2, the proximal seal 230, the proximal portion 312 of the attachment member 310, and the portion of the pusher conduit 214 therebetween form a substantially fluid-tight pressure chamber 234.

As shown in FIG. 1, the system 10 further includes a power supply 400 for supplying direct current to the positive and negative conductors 220, 222. Activation of the power supply 400 causes electrical current to flow in a circuit including the positive and negative conductors 220, 222 and the resistive heating coil 210. The power supply 400 preferably includes an onboard energy source, such as batteries (e.g., a pair of AAA batteries), along with drive circuitry 402. The drive circuitry 402 may include one or more microcontrollers or processors configured to output a driving current. The power supply 400 illustrated in FIG. 1 includes a receptacle 404 configured to receive and mate with the proximal end 202 of the delivery wire assembly 200. Upon insertion of the proximal end 202 into the receptacle 404, the positive, negative electrical contracts 216, 224 disposed on the delivery wire assembly 200 electrically couple with corresponding contacts (not shown) located in the power supply 400.

A visual indicator 406 (e.g., LED light) is used to indicate when the proximal end 202 of delivery wire assembly 200 has been properly inserted into the power supply 400. Another visual indicator 420 is activated if the onboard energy source needs to be recharged or replaced. The power supply 400 includes an activation trigger or button 408 that is depressed by the user to apply the electrical current to the resistive heating coil 210 via the positive and negative conductors 220, 222. Once the activation trigger 408 has been activated, the driver circuitry 402 automatically supplies current. The drive circuitry 402 typically operates by applying a substantially constant current, e.g., around 50-250 mA. A visual indicator 412 may indicate when the power supply 400 is supplying adequate current to the resistive heating coil 210.

In use, the vaso-occlusive coil 300 is attached to the pusher assembly 200 at junction 250. The attached vaso-occlusive coil 300 and pusher assembly 200 are threaded through the delivery catheter 100 to a target location (e.g., an aneurysm) in the patient's vasculature. Once the distal and 304 of the vaso-occlusive coil 300 reaches the target location, the vaso-occlusive coil 300 is pushed further distally until it's completely exits the distal and 104 of the delivery catheter 100.

In order to detach the vaso-occlusive coil 300 from the pusher assembly 200, the power supply 400 is activated by depressing the trigger 408. The drive circuitry 402 in the power supply 400 applies a current to the positive and negative conductors 220, 222 through the positive and negative electrical contacts 216, 224. As the applied current travels through the resistive heating coil 210, the resistive heating coil 210 generates heat. The generated heat raises the temperature of the pressure generating material 226 to the temperature at which it changes phases from solid 226*a* liquid and/or a gas 226*b*. The phase change and increased temperature increases the pressure inside of the substantially fluid-tight pressure chamber 234 defined by the proximal seal 230, the proximal portion 312 of the attachment member 310, and the portion of the pusher conduit 214 therebetween.

When the pressure inside of the pressure chamber 234 is sufficient to overcome the friction between the proximal portion 312 of the attachment member 310 and the proximal end of the pusher conduit 214, the attachment member 310 and the vaso-occlusive coil 300 attached thereto are ejected from the pusher assembly 200. This positive thrust force separating the vaso-occlusive coil 300 from the pusher assembly 200 ensures separation and prevents "sticky coils." The liquids and gases generated during detachment are readily and harmlessly absorbed into the blood.

Figure 3:
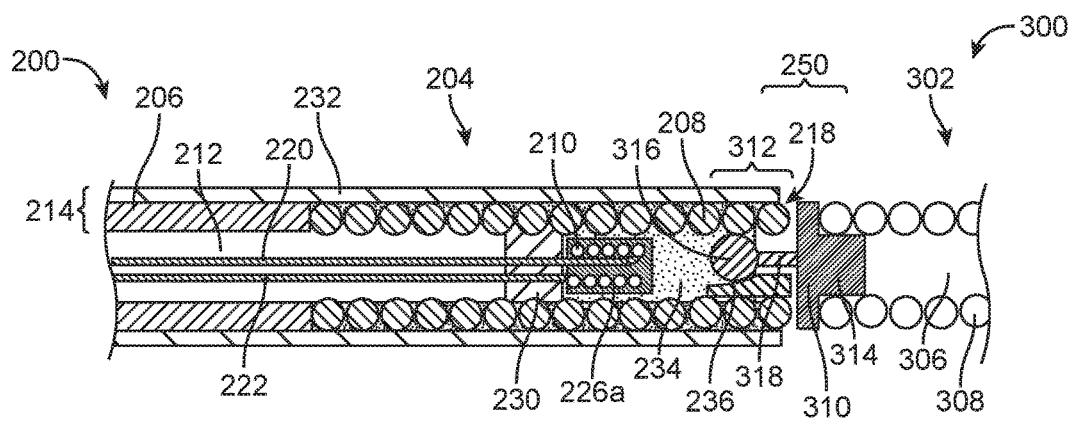

The vaso-occlusive device delivery system 10 depicted in FIG. 3 is very similar to the system 10 depicted in FIG. 2. Similar elements of this embodiment are identified with the same reference numbers as discussed above with respect to FIG. 2. The difference between the systems 10 depicted in these figures is the retention mechanism for the vaso-occlusive coil 300. The proximal portion 312 of the attachment member 310 depicted in FIG. 3 has a cross-sectional area smaller than the cross-sectional area of the pusher lumen 212.

In the system 10 depicted in FIG. 3, the proximal portion 312 includes a spherical member 316 connected to a stem 318. The spherical member 316 can be made of a non-compressible material. The pusher assembly 200 also includes a wedge 236 attached to an interior surface of the pusher conduit 214 in a distal end of the pusher lumen 212. The wedge 236 is also disposed between the spherical member 316 the interior surface on the of the pusher conduit 214. The wedge 236 can be made of a deformable polymer and can frictionally secure the spherical member 316, the attachment member 310, and therefore the vaso-occlusive coil 300 to the pusher assembly 200.

When the resistive heating coil 210 is activated as described above, pressure builds in the substantially fluid tight pressure chamber 234 defined in this embodiment by the proximal seal 230, the spherical member 316, the wedge 236, and the pusher conduit 214 therebetween. The increased pressure deforms the wedge 236 and ejects the spherical member 316 from the pusher assembly 200, as also described above. Ejecting the spherical member 316 detaches the vaso-occlusive coil 300 from the pusher assembly 200 with a thrust force.

Figure 4:
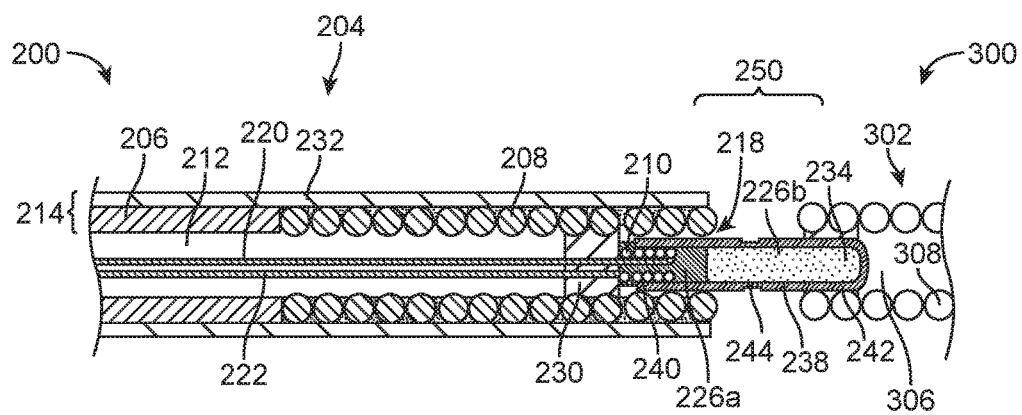

The vaso-occlusive device delivery system 10 depicted in FIG. 4 is similar to the systems 10 depicted in FIGS. 2 and 3. Similar elements of this embodiment are identified with the same reference numbers as discussed above with respect to FIGS. 2 and 3. The embodiment depicted in FIG. 4 has different retention and detachment mechanisms than those depicted in FIGS. 2 and 3. The vaso-occlusive coil 300 and pusher assembly 200 are attached by a tubular member 238 having an open proximal end 240 and a closed distal end 242. The tubular member 238 is part of the pusher assembly 200. The tubular member 238 forms a bore and may be made from polymers, metals, alloys and ceramics.

The open proximal end 240 of the tubular member 238 is disposed in the distal end of the pusher lumen 212 around the resistive heating coil 210 and the pressure generating material 226, effectively closing the proximal end 240 of the tubular member 238. The open proximal end 240 of the tubular member 238 may be attached to the pusher assembly 200 via the pusher conduit 214. The closed distal end 242 of the tubular member 238 is attached to the vaso-occlusive coil 300 in the proximal end of the vaso-occlusive coil lumen 306. While the closed distal end 242 of the tubular member 238 is attached to the vaso-occlusive coil 300, the tubular member 238 remains part of the pusher assembly 200.

The tubular member 238, the resistive heating coil 210, and the pressure generating material 226 form a substantially fluid-tight pressure chamber 234. When the resistive heating coil 210 is activated as described above, pressure builds in the pressure chamber 234, bursting/severing the tubular member 238 and detaching the vaso-occlusive coil 300 from the pusher assembly 200 with a positive thrust force. Optionally, a detachment zone 244 between the proximal and distal ends 240, 242 of the tubular member 238 may be treated to facilitate severing of the tubular member 238. In the embodiment depicted in FIG. 4, the detachment zone 244 is perforated. In other embodiments, the detachment zone 244 may be either thermally or mechanically treated to facilitate detachment.

Figure 5A:
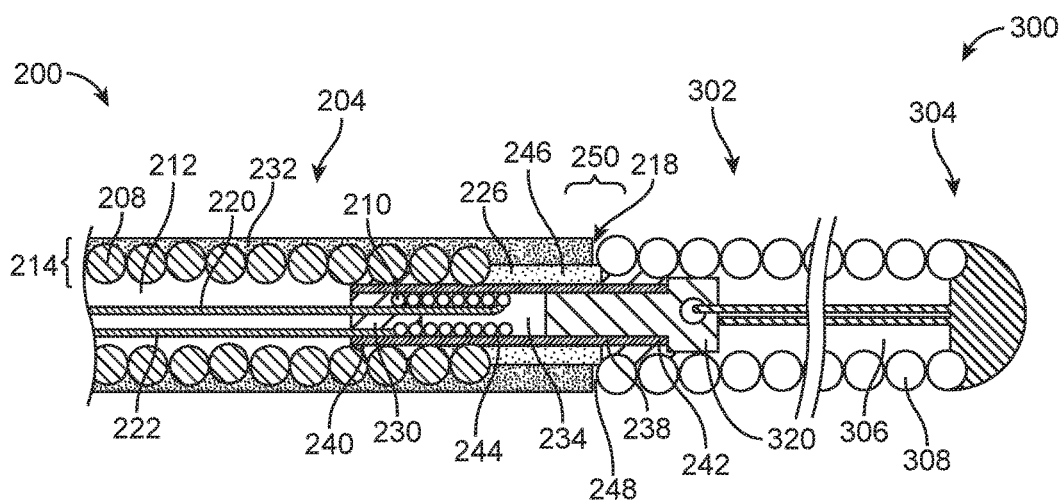
Figure 5B:
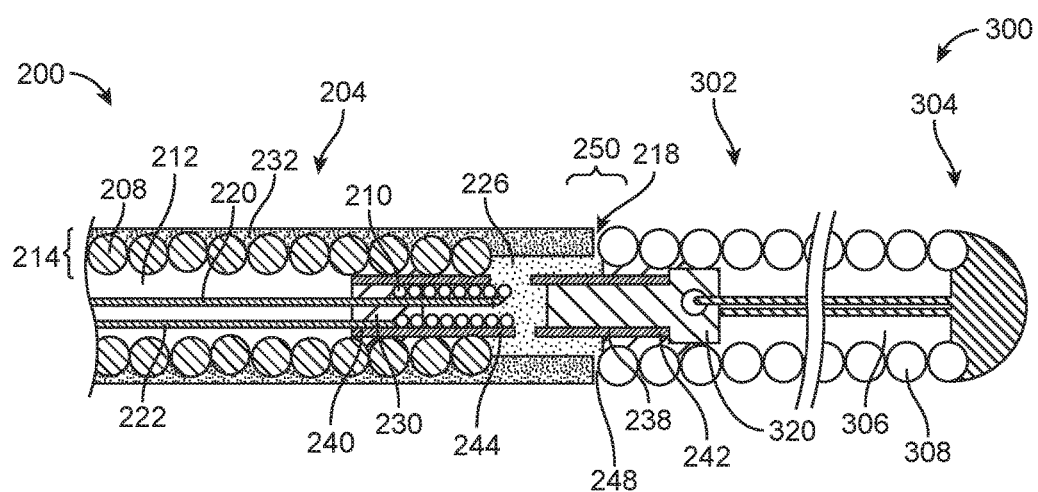

The embodiment depicted in FIGS. 5A and 5B is similar to the system 10 depicted in FIG. 4. Similar elements of this embodiment are identified with the same reference numbers as discussed above with respect to FIG. 4. The embodiment depicted in FIGS. 5A and 5B has different retention and detachment mechanisms than that depicted in FIG. 4. Like the embodiment depicted in FIG. 4, the vaso-occlusive coil 300 and pusher assembly 200 are attached by a tubular member 238, which is part of the pusher assembly 200. However, the tubular member 238 has proximal and distal ends 240, 242 that are both open and there is no solid pressure generating material surrounding the resistive heating coil 210.

The open proximal end 240 is disposed in the distal end of the pusher lumen 212 around the resistive heating coil 210 and the proximal seal 230, effectively closing the proximal end 240. The open distal end 242 is attached to the vaso-occlusive coil 300 in the proximal end of the vaso-occlusive coil lumen 306. The open distal end 242 is also disposed around an adapter 320, effectively closing the distal end 242.

The outer sleeve 232 extends distally beyond the distal coil portion 208 of the pusher conduit 214, almost making contact with vaso-occlusive coil 300. The distal end of the outer sleeve 232 the tubular member 238 and the distal end of the coil portion 208 form an annular space 246 with a small opening 248 therein. The small opening 248 connects the annular space with the environment exterior to the system 10. During delivery, a fluid (i.e., pressure generating material) 226 flows through the small opening 248 into the annular space 246. As the resistive heating coil 210 generates heat, the fluid 226 in the annular space 246 rapidly expands and/or undergoes a phase change becoming a gas. This increases the pressure in the annular space and severs the tubular member 238, thereby releasing the vaso-occlusive coil 300 from the pusher assembly 200 with positive thrust force (FIG. 5B).

The resistive heating coil 210 can also thermally degrade the tubular member 238, facilitating severance thereof. This thermal degradation is described in co-owned application Ser. No. 61/785,148, filed Mar. 14, 2013 also entitled "Vaso-Occlusive Device Delivery System". The contents of the application Ser. No. 61/785,148 are fully incorporated herein by reference as though set forth in full. Further, the proximal seal 230, the adapter 320, and the tubular member 238 therebetween form a substantially fluid-tight pressure chamber 234 separate from the annular space 246. When the resistive heating coil 210 generates heat, air in the pressure chamber 234 expands and facilitates severance of the tubular member 238.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A vaso-occlusive device delivery assembly, comprising:
   a pusher assembly including a substantially fluid tight pressure chamber in a distal end portion thereof;
   a thermally activated pressure generating material disposed in the pressure chamber;
   a heat generating member at least partially disposed in the pressure chamber, the heat generating member substantially surrounded by the pressure generating material; and
   a vaso-occlusive device detachably coupled to the pusher assembly distal of the pressure chamber, wherein the pressure generating material comprises a solid that is configured for changing state into, or otherwise releasing at least one of, a liquid or a gas that increases a pressure in the pressure chamber, thereby detaching the vaso-occlusive device from the pusher assembly, in direct response to heat generated by the heat generating member, wherein
   the vaso-occlusive device comprises an attachment member at a proximal end thereof, the attachment member being frictionally secured to the pusher assembly, wherein a proximal end of the attachment member comprises a distal wall of the pressure chamber, such that the increased pressure in the pressure chamber expels the attachment member from the pusher assembly.

2. The vaso-occlusive device delivery assembly of claim 1, the pusher assembly further comprising a resilient retaining member frictionally secured to the attachment member, wherein the increased pressure deforms the resilient retaining member.

3. The vaso-occlusive device delivery assembly of claim 2, wherein the resilient retaining member is made of a deformable polymer.

4. A vaso-occlusive device delivery assembly, comprising:
   a pusher assembly;
   a tubular connecting member at a distal end of the pusher assembly, the tubular connecting member at least partially defining a substantially fluid tight pressure chamber;
   a thermally activated pressure generating material disposed in the pressure chamber;
   a heat generating member at least partially disposed in the pressure chamber; and
   a vaso-occlusive device detachably coupled to the pusher assembly, a proximal end of the vaso-occlusive device attached to a distal end of the tubular connecting member, wherein a phase change in the pressure generating material, when heated by the heat generating member, occurs that increases a pressure in the pressure chamber, thereby directly causing detachment of the vaso-occlusive device from the pusher assembly.

5. The vaso-occlusive device delivery assembly of claim 4, wherein the pressure generating material is located adjacent to, or in contact with, the heat generating member.

6. The vaso-occlusive device delivery assembly of claim 4, wherein the pressure generating material comprises a solid.

7. The vaso-occlusive device delivery assembly of claim 6, wherein the pressure generating material comprises an inorganic salt hydrate selected from the group consisting of sodium carbonate monohydrate, calcium sulfate dihydrate, calcium sulfate pentahydrate, copper sulfate pentahydrate, and sodium bicarbonate.

8. The vaso-occlusive device delivery assembly of claim 4, wherein the heat generating member is a resistive heating coil.

9. The vaso-occlusive device delivery assembly of claim 4, the vaso-occlusive device comprising an attachment member at a proximal end thereof, the attachment member being frictionally secured to the pusher assembly, wherein a proximal end of the attachment member comprises a distal wall of the pressure chamber, such that the increased pressure in the pressure chamber expels the attachment member from the pusher assembly.

10. The vaso-occlusive device delivery assembly of claim 9, the pusher assembly further comprising a resilient retaining member frictionally secured to the attachment member, wherein the increased pressure deforms the resilient retaining member.

11. The vaso-occlusive device delivery assembly of claim 10, wherein the resilient retaining member is made of a deformable polymer.

12. The vaso-occlusive device delivery assembly of claim 4, wherein the tubular connecting member comprises a detach zone, such that the increased pressure ruptures the tubular connecting member in the detach zone, and wherein the detach zone is thermally or mechanically weakened.

13. The vaso-occlusive device delivery assembly of claim 4, wherein the heat generated by the heat generating member raises the temperature of the pressure generating material, such that the phase change in the pressure changing material occurs.

14. A vaso-occlusive device delivery assembly, comprising:
   a pusher assembly;

a tubular connecting member at a distal end of the pusher assembly, the tubular connecting member at least partially defining a substantially fluid tight pressure chamber;

a thermally activated pressure generating material disposed in the pressure chamber;

a heat generating member at least partially disposed in the pressure chamber; and a vaso-occlusive device detachably coupled to the pusher assembly via the tubular connecting member, wherein the pressure generating material, when heated by the heat generating member, increases a pressure in the pressure chamber, thereby rupturing the tubular connecting member and detaching the vaso-occlusive device from the pusher assembly.

15. The vaso-occlusive device delivery assembly of claim 14, wherein the pressure generating material is a single substance that changes state into, or otherwise releases at least one of, a liquid or a gas in response to heat generated by the heat generating member.

16. The vaso-occlusive device delivery assembly of claim 14, wherein the tubular connecting member comprises a detach zone, such that the increased pressure ruptures the tubular connecting member in the detach zone, and wherein the detach zone is thermally or mechanically weakened.

* * * * *